(12) United States Patent
Li et al.

(10) Patent No.: US 10,888,865 B2
(45) Date of Patent: Jan. 12, 2021

(54) DEVICE AND METHOD FOR SAMPLE COLLECTION

(71) Applicant: Coyote Bioscience Co., Ltd., Beijing (CN)

(72) Inventors: Xiang Li, Beijing (CN); Xiaobing Mu, Beijing (CN); Huiying Feng, Beijing (CN)

(73) Assignee: Coyote Bioscience Co., Ltd., Beijing (CN)

( * ) Notice: Subject to any disclaimer, the term of this patent is extended or adjusted under 35 U.S.C. 154(b) by 536 days.

(21) Appl. No.: 15/861,011

(22) Filed: Jan. 3, 2018

(65) Prior Publication Data
US 2018/0243736 A1     Aug. 30, 2018

Related U.S. Application Data

(63) Continuation of application No. PCT/CN2015/083894, filed on Jul. 13, 2015.

(51) Int. Cl.
*B01L 3/00*     (2006.01)
*G01N 1/02*     (2006.01)
(Continued)

(52) U.S. Cl.
CPC ............ *B01L 3/5029* (2013.01); *A61B 10/02* (2013.01); *B01L 3/523* (2013.01); *B01L 3/545* (2013.01);
(Continued)

(58) Field of Classification Search
None
See application file for complete search history.

(56) References Cited

U.S. PATENT DOCUMENTS 4,769,333 A     9/1988 Dole et al.
4,803,998 A *   2/1989 Kezes ................ A61B 10/0096
                                                435/307.1
(Continued)

FOREIGN PATENT DOCUMENTS

CN     101095614 A     1/2008
CN     101583393 A     11/2009
(Continued)

OTHER PUBLICATIONS

Co-pending U.S. Appl. No. 15/809,798, filed Nov. 10, 2017.
(Continued)

*Primary Examiner* — Jyoti Nagpaul
(74) *Attorney, Agent, or Firm* — Wilson Sonsini Goodrich & Rosati

(57) ABSTRACT

The present disclosure provides devices, methods and kits for collecting a sample of a subject for nucleic acid amplification. The device may comprise: a collection vessel that can include reagents necessary for nucleic acid amplification, wherein the collection vessel may be adapted to accept at least one swab containing a sample; a cap integrated with the collection vessel and having a channel extending therethrough to permit the at least one swab to be deposited in the collection vessel, wherein the channel is closable upon rotation of the cap; and at least one cutting member that severs a longitudinal portion of a stem of the swab extending through said channel upon rotation of the cap.

23 Claims, 4 Drawing Sheets

(51) Int. Cl.
  *A61B 10/02* (2006.01)
  *G01N 1/38* (2006.01)
  *G01N 33/487* (2006.01)
  *A61B 10/00* (2006.01)

(52) U.S. Cl.
  CPC .............. *G01N 1/02* (2013.01); *G01N 1/38* (2013.01); *G01N 33/48778* (2013.01); *A61B 10/007* (2013.01); *A61B 10/0051* (2013.01); *A61B 2010/0074* (2013.01); *A61B 2010/0216* (2013.01); *B01L 2200/0689* (2013.01); *B01L 2300/021* (2013.01); *B01L 2300/022* (2013.01); *B01L 2300/042* (2013.01); *B01L 2300/046* (2013.01); *B01L 2300/06* (2013.01); *G01N 2001/028* (2013.01); *G01N 2001/383* (2013.01); *G01N 2800/26* (2013.01)

(56) References Cited

U.S. PATENT DOCUMENTS

| | | | |
|---|---|---|---|
| 5,833,630 | A | 11/1998 | Kloth |
| 6,357,583 | B1 | 3/2002 | Rainen |
| 8,202,495 | B1 | 6/2012 | Smith |
| 2006/0094028 | A1 | 5/2006 | Danna et al. |
| 2009/0221893 | A1 | 9/2009 | Herndon |
| 2012/0016308 | A1 | 1/2012 | Schott |
| 2012/0282616 | A1 | 11/2012 | Zeijlstra et al. |
| 2014/0048510 | A1 | 2/2014 | Kilduff et al. |

FOREIGN PATENT DOCUMENTS

| | | |
|---|---|---|
| CN | 101835423 A | 9/2010 |
| CN | 203159612 U | 8/2013 |
| CN | 203307336 U | 11/2013 |
| CN | 103857469 A | 6/2014 |
| CN | 103945941 A | 7/2014 |
| CN | 104411243 A | 3/2015 |
| CN | 104582571 A | 4/2015 |
| EP | 1621886 A1 | 2/2006 |
| EP | 2269509 A1 | 1/2011 |
| EP | 2468341 A1 | 6/2012 |
| WO | WO-2014151996 A2 | 9/2014 |
| WO | WO-2014151996 A3 | 12/2014 |
| WO | WO-2015096063 A1 | 7/2015 |
| WO | WO-2015096763 A1 | 7/2015 |
| WO | WO-2016106717 A1 | 7/2016 |
| WO | WO-2016187780 A1 | 12/2016 |
| WO | WO-2016188430 A1 | 12/2016 |
| WO | WO-2017008228 A1 | 1/2017 |

OTHER PUBLICATIONS

Co-pending U.S. Appl. No. 15/809,839, filed Nov. 10, 2017.
PCT/CN2015/079706 International Search Report and Written Opinion dated Mar. 29, 2016.
PCT/CN2015/083894 International Search Report and Written Opinion dated Mar. 24, 2016.
PCT/CN2016/083295 International Search Report and Written Opinion dated Aug. 18, 2016.

* cited by examiner

DEVICE AND METHOD FOR SAMPLE COLLECTION

CROSS-REFERENCE

This application is a continuation of PCT Application Serial No. PCT/CN2015/083894, filed Jul. 13, 2015, which application is herein incorporated by reference in its entirety for all purposes.

BACKGROUND

Molecular diagnostics based on polymerase chain reaction (PCR) techniques have been widely used, e.g., in the detection of microorganisms and viruses. Samples (e.g., a blood sample) for use in laboratory testing are often obtained by way of venipuncture or through non-venous puncture, then, the samples are typically transferred to a laboratory for further processing and testing by service providers, e.g., a laboratory technician or a nurse. Samples are normally fractionated (e.g., by centrifugation), purified and processed to extract certain components or molecules therein, which may then be examined to reveal information suitable for diagnosis. The tests often involve amplifying and sequencing of nucleic acid molecules present in the samples, e.g., by PCR (e.g., qPCR).

SUMMARY

Although there are methods and systems currently available for the collection of biological samples from a subject, recognized herein are various limitations associated with such methods and systems. For example, normally, a relatively large quantity of sample may be required to obtain reliable test results, the transportation process can be lengthy, samples can get contaminated or deteriorated in the process, it may take days or even weeks to obtain test results, and expertise and professional experience may be required to conduct the test and/or interpret test results. Also, during the process of obtaining, transporting and testing of the samples, analyst (e.g., a nurse) can be at the risk of being infected by pathogens or viruses comprised in the sample. These may be problematic for both the subject to be tested and the analyst performing the test. Recognized herein is the need for devices and methods that enable fast, safe, and reliable molecular testing.

The present disclosure provides devices and methods for collecting a sample from a subject in a fast and simple manner, which makes it possible to perform on-site molecular diagnosis quickly and easily, while generating reliable result.

An aspect of the present disclosure provides a device for collecting a sample for nucleic acid amplification. The device may comprise a collection vessel that includes reagents necessary for nucleic acid amplification, wherein the collection vessel is adapted to accept at least one swab containing the sample; a cap integrated with the collection vessel and having a channel extending therethrough to permit the at least one swab to be deposited in said collection vessel, wherein said channel is closable upon rotation of the cap; and at least one cutting member that severs a longitudinal portion of a stem of the swab extending through the channel upon rotation of the cap. The collection vessel and/or the cap may be dimensioned such that upon depositing the swab in the collection vessel, the stem of the swab extends through the channel. In addition, upon rotation of the cap, the cutting member may sever a longitudinal portion of the stem of the swab extending through the channel to provide the swab sealed in the collection vessel and in contact with the reagents necessary for nucleic acid amplification. Rotation of the cap may provide a hermetic seal to the collection vessel. In some embodiments, the cutting member may be integrated with the cap.

In some embodiments, the stem of the swab includes a collar capable of engaging with the channel to provide the stem extending through the channel when the swab is deposited in the collection vessel.

In some embodiments, the cap includes a gasket that provides a seal to the collection vessel upon rotation of the cap.

In some embodiments, the cutting member includes at least one blade. In some cases, the cutting member may be in the channel. The blade may be rotatable with respect to a circumference of the channel. In some embodiments, the at least one blade may include at least 2 blades.

In some embodiments, the at least one swab includes at least 2 swabs, at least 3 swabs, at least 4 swabs, or at least 5 swabs. In some embodiments, the at least two swabs are integrated with the stem.

In some embodiments, rotation of the cap seals the channel. In certain cases, upon rotation of the cap to seal the channel, the cap moves towards the collection vessel.

In some embodiments, the collection vessel includes identifying information of the subject. The identifying information may be anonymous. The identifying information may be on a barcode. The identifying information may also be in a radio-frequency identification (RFID) tag.

In some embodiments, the reagents necessary for nucleic acid amplification include one or more primers and a polymerizing enzyme. The reagents may also include Mg or Mn ions. In some cases, the reagents may include one or more of the following: primer(s), probe(s), nucleotides (e.g., nucleotide triphosphates containing deoxyribose, or dNTP), polymerizing enzyme (or polymerase), reverse transcription enzyme (or reverse transcriptase), and/or amplification buffer. The reagents can include any one, two, three, four, five, or all of the primer(s), probe(s), nucleotides, polymerizing enzyme, reverse transcription enzyme and amplification buffer. The one or more primers may have sequences that are selected to assay for a presence of a disorder or disease, such as an infectious disease, in the subject.

Another aspect of the present disclosure provides a method for collecting a biological sample from a subject for nucleic acid amplification. The method may comprise: (a) providing a collection device comprising (i) a collection vessel that includes reagents necessary for nucleic acid amplification, wherein the collection vessel is adapted to accept at least one swab containing the biological sample, (ii) a cap integrated with the collection vessel and having a channel extending therethrough to permit the at least one swab to be deposited in the collection vessel, wherein the channel is closable upon rotation of the cap, and (iii) at least one cutting member that severs a longitudinal portion of a stem of the swab extending through the channel upon rotation of the cap, wherein the collection vessel and/or the cap are dimensioned such that upon depositing the swab in the collection vessel, the stem of the swab extends through the channel; (b) depositing the swab having the biological sample from the subject in the collection vessel, and (c) rotating the cap, wherein upon rotation of the cap, the cutting member severs a longitudinal portion of the stem of the swab extending through the channel to provide the swab sealed in the collection vessel and in contact with the reagents necessary for nucleic acid amplification.

In some embodiments, the method further comprises performing the nucleic acid amplification on the biological sample or a nucleic acid sample derived from the biological sample. Performing the nucleic acid amplification may comprise subjecting a reaction mixture having the biological sample or the nucleic acid sample to nucleic acid amplification conditions comprising at least one heating and cooling cycle.

In some embodiments, the nucleic acid amplification conditions comprises cycling a temperature of a reaction mixture having the biological sample or the nucleic acid sample between at least two different temperatures. In some embodiments, the nucleic acid amplification conditions comprise cycling a temperature of a reaction mixture having the biological sample or the nucleic acid sample between at least three different temperatures. In some embodiments, the nucleic acid amplification conditions comprise cycling a temperature of a reaction mixture having the biological sample or the nucleic acid sample between a denaturing temperature, annealing temperature and elongation temperature.

Another aspect of the present disclosure provides a kit for nucleic acid amplification. The kit may comprise: a collection device comprising (i) a collection vessel that includes reagents necessary for nucleic acid amplification, wherein the collection vessel is adapted to accept at least one swab, (ii) a cap integrated with the collection vessel and having a channel extending therethrough to permit the at least one swab to be deposited in the collection vessel, wherein the channel is closable upon rotation of the cap, and (iii) at least one cutting member that severs a longitudinal portion of a stem of the at least one swab extending through the channel upon rotation of the cap, wherein the collection vessel and/or the cap are dimensioned such that upon depositing the at least one swab in the collection vessel, the stem of the swab extends through the channel. The kit may also comprise instructions that permit a user to (a) collect a biological sample from a source of the sample using the at least one swab, and (b) deposit the at least one swab having the biological sample into the collection vessel to provide a reaction mixture comprising the biological sample and the reagents necessary for nucleic acid amplification.

In some embodiments, the instructions permit the user to perform nucleic acid amplification using the biological sample. The instructions may also permit the user to perform (a) and (b) in a time period that is less than about 1 minute, or less than about 30 seconds.

In some embodiments, the kit further includes the at least one swab.

In some cases, the user may be a healthcare professional. For example, the user is a primary physician or laboratory technician.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 4 (panels B and C) provide enlarged views of a cross section of a cap.

DETAILED DESCRIPTION

Figure 1:
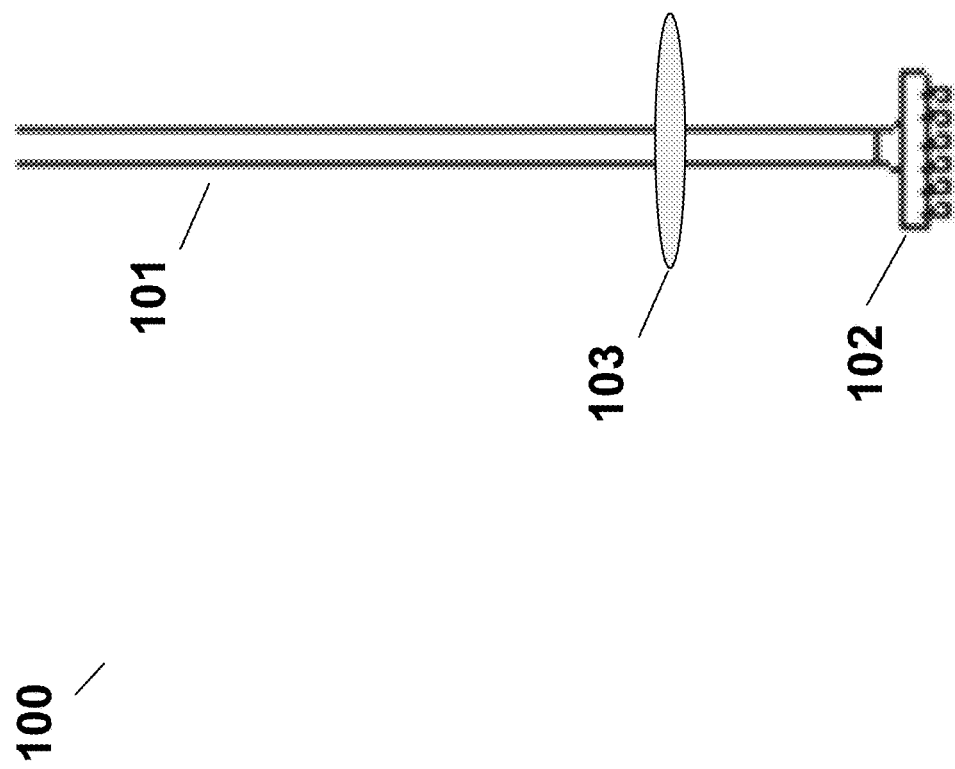
FIG. 1 schematically illustrates a swab of the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sample," as used herein, generally refers to a tissue sample, a bodily fluid sample, cells or other biological samples. For example, a sample can be but is not limited to tissues or cells obtainable from nose, pharynx, ear, eye, throat, mouth, bucca, cervix, vagina, skin wound, urethra or other body parts of a subject. In some examples, the sample is a blood sample, urine sample, or saliva sample. The sample may be a fluid sample, a solid sample and/or a semi-solid sample. When the sample is a tissue sample of a subject, it may be obtainable from e.g., connective tissue, muscle tissue, nervous tissue, epithelial tissue, cartilage, cancerous tissue, bone or other tissue.

A sample may contain or be suspected of containing biological material, such as a nucleic acid molecule or protein. The biological material may be from a subject or may be from a pathogen (e.g., bacteria or virus) residing in or on the subject. The sample can include cellular material. The sample can include nucleic acid material, such as deoxyribonucleic acid (DNA) or ribonucleic acid (RNA). The sample can include protein(s). For example, a subject sample can be a biological sample containing one or more nucleic acid molecules and/or proteins. The biological sample can be obtained or obtainable (e.g., extracted or isolated) from a tissue and/or cell sample of a subject that can be selected from tissues and/or cells from nose, pharynx, ear, eye, throat, mouth, bucca, cervix, vagina, skin wound, urethra of a subject. In some other examples, the sample may be an environmental sample (e.g., soil, waste, ambient air and etc.), industrial sample (e.g., samples from any industrial processes), and food samples (e.g., dairy products, vegetable products, and meat products).

A subject may provide a sample, and/or the sample may be collected from a subject. The sample may be collected from a living subject or a dead subject. The sample may be collected fresh from a subject or may have gone through some form of pre-processing, storage, or transport.

One or more, two or more, three or more, four or more, five or more, six or more, seven or more, eight or more, ten or more, twelve or more, fifteen or more, or twenty or more different types of samples may be collected from a subject. A single type of sample or a plurality of types of samples may be collected from the subject simultaneously or at different times. A sample may be collected by the subject or by another individual, such as a healthcare professional (e.g., primary physician or laboratory technician).

The term "point of care," as used herein, generally refers to locations where a subject may be cared for (e.g., by testing, monitoring, treatment, diagnosis, guidance, sample collection, identification (ID) verification, medical services, non-medical services, etc.), and may include, but not limited to, a subject's home, a subject's business, the location of a healthcare provider (e.g., doctor), hospitals, emergency rooms, operating rooms, clinics, health care professionals' offices, laboratories, retailers—e.g., pharmacies (e.g., retail pharmacy, clinical pharmacy, hospital pharmacy), drugstores, supermarkets, grocers, etc.—transportation vehicles (e.g., car, boat, truck, bus, airplane, motorcycle, ambulance, mobile unit, fire engine/truck, emergency vehicle, law enforcement vehicle, police car, or other vehicle configured to transport a subject from one point to another, etc.), traveling medical care units, mobile units, schools, day-care centers, security screening locations, combat locations, health assisted living residences, government offices, office buildings, tents, sample acquisition sites (e.g., blood collection centers), or any other point of care location described elsewhere in the present application. The point of care may be a location that is stationary or movable.

The term "swab," as used herein, generally refers to an element or unit attached to an end of a support member (e.g., rod or stem) capable of obtaining and/or retaining a sample, e.g., a biological sample. For example, a swab can be a wad of material (e.g., absorbent material) wound around an end of a support member (e.g., a rod or stem). As another example, a swab can be in the form of a short brush attached to an end of a support member (e.g., a rod or stem). A swab may be made of any material (e.g., sponge, cloth patch, cotton, nylon) in any shape or dimension suitable for obtaining and/or maintaining a sample, e.g., a biological sample from a subject. A swab may be made of a fibrous material, such as natural fiber, semi-synthetic fiber, synthetic fiber, etc. Examples of the fibrous material may include but not limited to: cotton, hemp, jute, flax, ramie, sisal, bagasse, banana, wood, animal (e.g., silk, sinew, catgut, wool, hair, fur), nylon, dacron, rayon or other cellulose fibers, metallic fiber, etc.

The term "channel," as used herein, generally refers to a path through which other element may go through. The channel may be kept in an open or a closed state, or be capable of switching between an open and a closed state. Dimensions of the channel may be variable and can be adjusted according to specific needs. In some examples, a channel may have a cross-sectional area that is no greater than about 10 square centimeters ($cm^2$), 9 $cm^2$, 8 $cm^2$, 7 $cm^2$, 6 $cm^2$, 5 $cm^2$, 4 $cm^2$, 3.5 $cm^2$, 3 $cm^2$, 2.5 $cm^2$, 2 $cm^2$, 1.5 $cm^2$, 1 $cm^2$, 0.9 $cm^2$, 0.8 $cm^2$, 0.7 $cm^2$, 0.6 $cm^2$, 0.5 $cm^2$, 0.4 $cm^2$, 0.3 $cm^2$, 0.2 $cm^2$, 0.1 $cm^2$, 0.07 $cm^2$, 0.05 $cm^2$, 0.03 $cm^2$, 0.02 $cm^2$, 0.01 $cm^2$. The cross-sectional area may vary or may remain the same along the length of the channel.

The term "cap," as used herein, generally refers to an overlying element or unit that is capable of covering a collection vessel. A cap can comprise screw structures to be mounted onto the collection vessel. The cap can have a shape that is compatible with the collection vessel. The cap can enable the collection vessel to be sealed, such as hermetically sealed. The cap may be penetrable.

The term "cutting member," as used herein, generally refers to any element comprising a cutting edge or side that is capable of severing a support member (e.g., rod or stem) of a swab, such as by cutting through a longitudinal portion of the support member. The cutting member may apply sufficient pressure to the support member to cause the support member to deform, in some cases break. For example, a cutting member may be a blade or an element comprising at least one blade. A cutting member can be formed of a polymeric material or metallic material, e.g., stainless steel, carbon steel, alloy steel, polycarbonate, ceramics, glass, etc.

The term "gasket," as used herein, generally refers to a sealing element capable of filling a space between two or more mating surfaces. A gasket may be able to prevent movement of material (e.g., leakage) from or into the joined objects while under compression. A gasket may be made from a material that is able to deform and tightly fill the space it is designed for, including any slight irregularities. For example, suitable material for making a gasket may include but not limited to paper, rubber, silicone, metal, cork, felt, neoprene, nitrile rubber, fiberglass, polytetrafluoroethylene (also known as PTFE or Teflon) and other polymeric materials, such as a plastic polymer (e.g., polychlorotrifluoroethylene).

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), or variants thereof. A nucleotide can include A, C, G, T or U, or variants thereof including but not limited to peptide nucleic acid (PNA). A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded. A nucleic acid may comprise one or more modified nucleotides, e.g., methylated nucleotides and nucleotide analogs.

The term "polymerase," as used herein, generally refers to any enzyme capable of catalyzing a polymerization reaction. The enzyme can be a polymerizing enzyme. Examples of polymerases include, without limitation, a nucleic acid polymerase, a transcriptase or a ligase. A polymerase can be a polymerization enzyme, a polymerizing enzyme and/or a reverse transcriptase.

The term "subject," as used herein, generally refers to a human, an animal or other organism (e.g., a plant). The subject may be a mammal, vertebrate, such as murines, simians, humans, farm animals, sport animals, or pets. The subject may be living or dead. The subject may be a patient, clinical subject, or pre-clinical subject. A subject may be undergoing diagnosis, treatment, monitoring, and/or disease prevention. The subject may or may not be under the care of a health care professional. The subject may be a person of any age, e.g., an infant, a toddler, an adult or an elderly.

The present disclosure provides devices, methods and systems for obtaining, processing and analyzing a sample. Various aspects of the devices, systems and methods described herein may be applied to any of the particular devices, systems and methods set forth below. Devices, systems and methods provided herein may be applied as a standalone device, system or method, or as part of an integrated system, e.g., in a system involving point of care services. In some embodiments, a system may include external amplification and/or sequencing devices (e.g., a PCR machine) or be integrated with external peripherals for integrated tests or services.

Device for Collecting a Sample of a Subject for Nucleic Acid Amplification

An aspect of the present disclosure provides a device for collecting a sample (e.g., a tissue sample, such as a sample comprising oral epithelial cells) of a subject for nucleic acid amplification. The device may comprise a collection vessel that can include reagents necessary for nucleic acid amplification. Such reagents may include one or more primers and one or more polymerizing enzymes. In certain cases, the reagents may comprise Mg or Mn ions. The reagents may include one or more of the following: primer(s), probe(s), nucleotides (e.g., nucleotide triphosphates containing deoxyribose, or dNTP), polymerizing enzyme (or polymerase), reverse transcription enzyme (or reverse transcriptase), and/or amplification buffer. The reagents can include any one, two, three, four, five, or all of the primer(s), probe(s), nucleotides, polymerizing enzyme, reverse transcription enzyme and amplification buffer. The primer(s) may have sequences that are selected to assay for a presence of a disorder or disease, such as an infectious disease, in the subject.

The collection vessel may be adapted to accept at least one swab containing the sample. In principle, the collection vessel may have any shape or size. For example, the collection vessel may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length. In some examples, the collection vessel may have a cross-sectional area of less than or equal to about 25 $cm^2$, 20 $cm^2$, 16 $cm^2$, 10 $cm^2$, 9 $cm^2$, 8 $cm^2$, 7 $cm^2$, 6 $cm^2$, 5 $cm^2$, 4 $cm^2$, 3 $cm^2$, 2.5 $cm^2$, 2 $cm^2$, 1.5 $cm^2$, 1 $cm^2$, 0.9 $cm^2$, 0.8 $cm^2$, 0.7 $cm^2$, 0.6 $cm^2$, 0.5 $cm^2$, 0.4 $cm^2$, 0.3 $cm^2$, 0.2 $cm^2$, or 0.1 $cm^2$. The cross-sectional area may vary or may remain the same along the length. In some examples, the collection vessel may have a length of less than or equal to about 20 centimeters (cm), 15 cm, 12 cm, 10 cm, 9 cm, 8 cm, 7 cm, 6 cm, 5 cm, 4 cm, 3 cm, 2.5 cm, 2 cm, 1.5 cm, 1 cm, 0.5 cm, or 0.1 cm.

The device may further comprise a cap, which may be made with an opaque, transparent, or translucent material. The cap may be fitted over the collection vessel or at least over a portion thereof. The cap may be integrated with the collection vessel. In some examples, the cap or a part thereof may be detachable from the collection vessel. For instance, the cap may be completely separable from the collection vessel, or with a portion remain connected to or mounted on the collection vessel, e.g., with a portion of the cap being hinged or otherwise linked to the collection vessel, or with a portion of the cap being mounted on the collection vessel while the other portion(s) being removed from the collection vessel. The cap may cover a portion of the collection vessel containing the reagents necessary for nucleic acid amplification. When the cap is in place, it may prevent material, such as air, fluid, or particulates, from entering the collection vessel.

The cap may be mounted or attached to the collection vessel in various ways. For example, the cap may snap-fit, twist on, friction-fit, clamp on, be magnetically attached, be screwed on, be tied in, being attached via elastic material (e.g., a rubber band). The attachment and/or mounting may be reversible and hence the cap may be removable from the collection vessel.

The cap may form a fluid-tight seal with the collection vessel, for example, when desired, the cap may provide a hermetic seal to the collection vessel. The cap may be an integrated one-piece element or may comprise two or more separable elements. For example, the cap may comprise two elements separable from each other, with a first element capable of being mounted on the collection vessel and a second element capable of being engaged with (e.g., being screwed onto) the first element, thereby sealing the collection vessel.

The cap may have a shape and size compatible with the collection vessel, so that it is capable of sealing the collection vessel when desired. For example, the cap may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length of the cap. In some examples, the cap may have a cross-sectional area of less than or equal to about 25 $cm^2$, 20 $cm^2$, 16 $cm^2$, 10 $cm^2$, 9 $cm^2$, 8 $cm^2$, 7 $cm^2$, 6 $cm^2$, 5 $cm^2$, 4 $cm^2$, 3 $cm^2$, 2.5 $cm^2$, 2 $cm^2$, 1.5 $cm^2$, 1 $cm^2$, 0.9 $cm^2$, 0.8 $cm^2$, 0.7 $cm^2$, 0.6 $cm^2$, 0.5 $cm^2$, 0.4 $cm^2$, 0.3 $cm^2$, 0.2 $cm^2$, or 0.1 $cm^2$. The cross-sectional area may vary or may remain the same along the length of the cap. In some examples, the cap may have a length of less than or equal to about 10 centimeter (cm), 9 cm, 8 cm, 7 cm, 6 cm, 5 cm, 4 cm, 3 cm, 2.5 cm, 2 cm, 1.9 cm, 1.8 cm, 1.7 cm, 1.6 cm, 1.5 cm, 1.4 cm, 1.3 cm, 1.2 cm, 1.1 cm, 1 cm, 0.9 cm, 0.8 cm, 0.7 cm, 0.6 cm, 0.5 cm, 0.4 cm, 0.3 cm, 0.2 cm, or 0.1 cm.

The cap may have a channel extending through the cap to permit the at least one swab to be deposited in the collection vessel. The channel may be opened and closed upon rotation of the cap. For example, the channel may be opened by rotating the cap (e.g., rotating clockwise), thereby the at least one swab may be inserted or otherwise deposited into the collection vessel through the open channel. When it is desired to close the channel, the cap may be rotated reversely (e.g., rotated counter clockwise). The channel may have a shape and size compatible with the swab and/or the cap, so that the at least one swab is permitted to get through the channel in the cap and being deposited into the collection vessel. For example, the channel may have a circular, elliptical, triangular, quadrilateral (e.g., square, rectangular, trapezoidal), pentagonal, hexagonal, octagonal, or any other cross-sectional shape. The cross-sectional shape may remain the same or may vary along the length of the channel. In some examples, the channel may have a cross-sectional area of less than or equal to about 25 $cm^2$, 20 $cm^2$, 16 $cm^2$, 10 $cm^2$, 9 $cm^2$, 8 $cm^2$, 7 $cm^2$, 6 $cm^2$, 5 $cm^2$, 4 $cm^2$, 3 $cm^2$, 2.5 $cm^2$, 2 $cm^2$, 1.5 $cm^2$, 1 $cm^2$, 0.9 $cm^2$, 0.8 $cm^2$, 0.7 $cm^2$, 0.6 $cm^2$, 0.5 $cm^2$, 0.4 $cm^2$, 0.3 $cm^2$, 0.2 $cm^2$, 0.1 $cm^2$, 0.07 $cm^2$, 0.05 $cm^2$, 0.03 $cm^2$, 0.02 $cm^2$, or 0.01 $cm^2$. The cross-sectional area may vary or may remain the same along the length. In some examples, the channel may have a length of less than or equal to about 10 cm, 9 cm, 8 cm, 7 cm, 6 cm, 5 cm, 4 cm, 3 cm, 2.5 cm, 2 cm, 1.9 cm, 1.8 cm, 1.7 cm, 1.6 cm, 1.5 cm, 1.4 cm, 1.3 cm, 1.2 cm, 1.1 cm, 1 cm, 0.9 cm, 0.8 cm, 0.7 cm, 0.6 cm, 0.5 cm, 0.4 cm, 0.3 cm, 0.2 cm, or 0.1 cm.

The device may also comprise at least one cutting member. The cutting member may be integrated with the cap (e.g., the cutting member may form a part of the cap). The cutting member may be capable of severing a support member (e.g., a stem) of the swab extending through the channel (e.g., a longitudinal portion of the stem) upon rotation of the cap, or apply a force or pressure that subjects the support member to bending such that the support member bends, deforms or is severed. For example, after the at least one swab is deposited into the collection vessel at an appropriate position (e.g., upon contacting of the swab with the reagents contained in the collection vessel), the cap may be rotated reversely (e.g., rotated counter clockwise), thereby the cutting member comprised in the cap may contact with and sever the stem of the swab. When the portion of the swab stem extending beyond the cap is severed, the cap may be further rotated counter clockwise, so that the remaining part of the swab may be sealed within the collection vessel while being in contact with the reagents necessary for nucleic acid amplification. The rotation of the cap may also provide a hermetic seal to the collection vessel. In some examples, the support member (e.g., a stem) of the swab has a hollow structure. In some examples, the cutting member may be a blade or an element comprising at least one blade. A cutting member can be formed of a polymeric material or metallic material, e.g., stainless steel, carbon steel, alloy steel, polycarbonate, ceramics, glass, etc. When the channel is open to permit the at least one swab to pass through, the cutting member may be retracted (e.g., by moving towards the wall of the channel and/or moving away from the cross-sectional center of the channel). Movement of the cutting member may be controlled or actuated with rotation of the cap. For example, when the cap is rotated clockwise, the cutting member may be actuated to retract away from the cross-sectional center of the channel and when the cap is rotated counter clockwise, the cutting member may be actuated to extend towards the cross-sectional center of the channel.

The collection vessel and/or the cap may be dimensioned such that upon depositing the swab in the collection vessel, the stem of the swab can extend through the channel. For example, the stem of the swab may include a collar capable of engaging with the channel to provide the stem extending through the channel when the swab is deposited in the collection vessel. The collar may be fixed or fixable onto the stem of the swab. In an example, the collar may assist in securing the swab at a particular position along the length of the collection vessel (e.g., a position where the head of the swab may be in contact with or immersed in the reagents contained in the collection vessel) by engaging with the channel. For example, the collar may engage with the channel by contacting with and pressing against the wall of the channel (e.g., applying a force to the wall of the channel in a direction roughly perpendicular to the direction of movement of the swab), thereby a frictional force may be created at the interface between the collar and the channel wall, which in turn may block further movement of the swab along the length of the channel. In another example, the collar may engage with the channel by having a cross-sectional area larger than that of an opening at an end of the channel (e.g., the end of the channel closer to the collection vessel), so that the collar cannot pass through said opening due to its larger cross-sectional area, which in turn may block further movement of the swab comprising the collar.

In some embodiments, the cap may include a gasket that provides a seal to the collection vessel upon rotation of the cap. The seal may be a hermetic seal. The gasket may be in any suitable shape or dimension capable of sealing the collection vessel. For example, the gasket can be in the form of an o-ring. The gasket may be made from a material that is able to deform and tightly fill the space it is designed for, including any slight irregularities. For example, suitable material for making a gasket may include but not limited to paper, rubber, silicone, metal, cork, felt, neoprene, nitrile rubber, fiberglass, polytetrafluoroethylene (also known as PTFE or Teflon) and other polymeric materials, such as a plastic polymer (e.g., polychlorotrifluoroethylene).

The cutting member may include at least one blade. The blade can be a metallic blade, such as a stainless steel blade. In some cases, the cutting member may be in the channel. The at least one blade may be rotatable with respect to a circumference of the channel. The at least one blade may include one or more blades, e.g., at least 2 blades, at least 3 blades, at least 4 blades, at least 5 blades, at least 6 blades, etc. The at least one blade may be rotatable by at least about 1 degree, 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees, 240 degrees, or 300 degrees.

The at least one swab may include one or more swabs, e.g., at least 2 swabs, at least 3 swabs, at least 4 swabs, at least 5 swabs, etc. When there are two or more swabs, the swabs may be integrated with the stem. When there are two or more swabs, each of the two or more swabs may be integrated with the same stem via a separate rod projecting from the stem, therefore, one end of the rod may be connected to the stem while the other end of the rod may be connected to a swab.

Rotation of the cap may seal the channel. For example, upon rotation of the cap along one direction (e.g., clockwise) to seal the channel, the cap may move towards the collection vessel. Upon rotation of the cap along an opposite direction (e.g., counter clockwise), the cap may move away from the collection vessel, which can open the cap such that it (or a portion thereof, such as one element of the cap) can be removed away from the collection vessel.

The collection vessel may include identifying information of the subject, which may be useful in revealing the identity of the subject. The identifying information can be anonymous. The identifying information may be on a barcode. The barcode can include a string of characters, e.g., letters and/or numbers. The identifying information may also be in a radio-frequency identification (RFID) tag.

In some embodiments, the collection device may be sealed with a sealing member (e.g., a plug) before a swab is deposited in the collection vessel. For example, the sealing member may be comprised in the cap (e.g., forming a part of the cap, for example, being inserted into the channel comprised by the cap). When the sealing member is in place, the channel may be closed and the cap may be sealed and contents contained in the collection vessel (e.g., reagents necessary for nucleic acid amplification) will be kept away from the surrounding environment (e.g., substances in the air, potential contaminants). When a swab is to be deposited in the collection vessel, the sealing member may be removed (e.g., being pulled away from the cap) so as to open the channel in the cap, thereby permitting the swab to be inserted into the collection vessel through the open channel. The sealing member may be made from a variety of materials, such as paper, rubber, silicone, metal, cork, felt, neoprene, nitrile rubber, fiberglass, polytetrafluoroethylene (also known as PTFE or Teflon) or other polymeric materials, such as a plastic polymer (e.g., polychlorotrifluoroethylene).

The collection vessel can have a volume of less than about 1 liter (L). For example, the collection vessel may have a volume of less than or equal to about 0.9 L, 0.8 L, 0.7 L, 0.6 L, 0.5 L, 0.4 L, 0.3 L, 0.2 L, 0.1 L, 0.05 L, 0.04 L, 0.03 L, 0.02 L, 0.01 L, 9 milliliter (ml), 8 ml, 7 ml, 6 ml, 5 ml, 4 ml, 3 ml, 2 ml, 1 ml, 0.9 ml, 0.8 ml, 0.7 ml, 0.6 ml, 0.5 ml, 0.4 ml, 0.3 ml, 0.2 ml, 0.1 ml, 0.09 ml, 0.08 ml, 0.07 ml, 0.06 ml, 0.05 ml, 0.04 ml, 0.03 ml, 0.02 ml, or 0.01 ml. The collection vessel can accept a sample volume of less than about 1 L. For example, the sample volume may be less than or equal to about 0.5 L, 0.4 L, 0.3 L, 0.2 L, 0.1 L, 0.05 L, 0.04 L, 0.03 L, 0.02 L, 0.01 L, 9 ml, 8 ml, 7 ml, 6 ml, 5 ml, 4 ml, 3 ml, 2 ml, 1 ml, 0.9 ml, 0.8 ml, 0.7 ml, 0.6 ml, 0.5 ml, 0.4 ml, 0.3 ml, 0.2 ml, 0.1 ml, 0.09 ml, 0.08 ml, 0.07 ml, 0.06 ml, 0.05 ml, 0.04 ml, 0.03 ml, 0.02 ml, 0.01 ml, 0.005 ml, or 0.001 ml. The collection vessel can contain reagents in a reagent volume of less than about 1 L. For example, the reagent volume may be less than or equal to about 0.5 L, 0.4 L, 0.3 L, 0.2 L, 0.1 L, 0.05 L, 0.04 L, 0.03 L, 0.02 L, 0.01 L, 9 ml, 8 ml, 7 ml, 6 ml, 5 ml, 4 ml, 3 ml, 2 ml, 1 ml, 0.9 ml, 0.8 ml, 0.7 ml, 0.6 ml, 0.5 ml, 0.4 ml, 0.3 ml, 0.2 ml, 0.1 ml, 0.09 ml, 0.08 ml, 0.07 ml, 0.06 ml, 0.05 ml, 0.04 ml, 0.03 ml, 0.02 ml, 0.01 ml, 0.005 ml, 0.001 ml, 0.0005 ml, or 0.0001 ml.

FIG. 1 shows a swab 100 that can be used with a collection device of the present disclosure. The swab 100 may comprise a head 102 attached to one end of a stem 101. The head may be in the form of a short brush made of a variety of materials, such as, e.g., nylon. The stem 101 may also include a collar 103 capable of engaging with a channel in a cap of the collection device to provide the stem extending through the channel when the swab is deposited in a collection vessel. The collar 103 may be fixed or fixable onto the stem 101, for example, the collar 103 may be irreversibly glued onto the stem 101. In another example, the collar 103 may be movable along the stem 101 and may be fixed at a particular position of the stem 101 by being reversibly clipped or fastened thereon. The collar 103 may be of any shape or dimension suitable for fixing the swab in a position within the collection vessel (for example, by engaging with a channel in a cap) so that the stem of the swab extends through the channel and the swab head containing a sample to be analyzed can be accessed by reagents contained in the collection vessel. In some examples, the stem 101 of the stab may have a cross-sectional area of less than or equal to about 25 cm$^2$, 20 cm$^2$, 16 cm$^2$, 10 cm$^2$, 9 cm$^2$, 8 cm$^2$, 7 cm$^2$, 6 cm$^2$, 5 cm$^2$, 4 cm$^2$, 3 cm$^2$, 2.5 cm$^2$, 2 cm$^2$, 1.5 cm$^2$, 1 cm$^2$, 0.9 cm$^2$, 0.8 cm$^2$, 0.7 cm$^2$, 0.6 cm$^2$, 0.5 cm$^2$, 0.4 cm$^2$, 0.3 cm$^2$, 0.2 cm$^2$, 0.1 cm$^2$, 0.07 cm$^2$, 0.05 cm$^2$, 0.03 cm$^2$, 0.02 cm$^2$, or 0.01 cm$^2$. The cross-sectional area may vary or may remain the same along the length of the stem 101. In some examples, the stem 101 may have a length of less than or equal to about 10 cm, 9 cm, 8 cm, 7 cm, 6 cm, 5 cm, 4 cm, 3 cm, 2.5 cm, 2 cm, 1.9 cm, 1.8 cm, 1.7 cm, 1.6 cm, 1.5 cm, 1.4 cm, 1.3 cm, 1.2 cm, 1.1 cm, 1 cm, 0.9 cm, 0.8 cm, 0.7 cm, 0.6 cm, 0.5 cm, 0.4 cm, 0.3 cm, 0.2 cm, or 0.1 cm. In some examples, the head 102 of the stab may have a cross-sectional area of less than or equal to about 25 cm$^2$, 20 cm$^2$, 16 cm$^2$, 10 cm$^2$, 9 cm$^2$, 8 cm$^2$, 7 cm$^2$, 6 cm$^2$, 5 cm$^2$, 4 cm$^2$, 3 cm$^2$, 2.5 cm$^2$, 2 cm$^2$, 1.5 cm$^2$, 1 cm$^2$, 0.9 cm$^2$, 0.8 cm$^2$, 0.7 cm$^2$, 0.6 cm$^2$, 0.5 cm$^2$, 0.4 cm$^2$, 0.3 cm$^2$, 0.2 cm$^2$, 0.1 cm$^2$, 0.07 cm$^2$, 0.05 cm$^2$, 0.03 cm$^2$, 0.02 cm$^2$, or 0.01 cm$^2$. The head 102 may have a cross-sectional area larger or smaller than that of the stem 101. In some examples, the head 102 may have a cross-sectional area equal to that of the stem 101. The collar 103 may have a cross-sectional area larger than that of both the head 102 and the stem 101.

Figure 2:
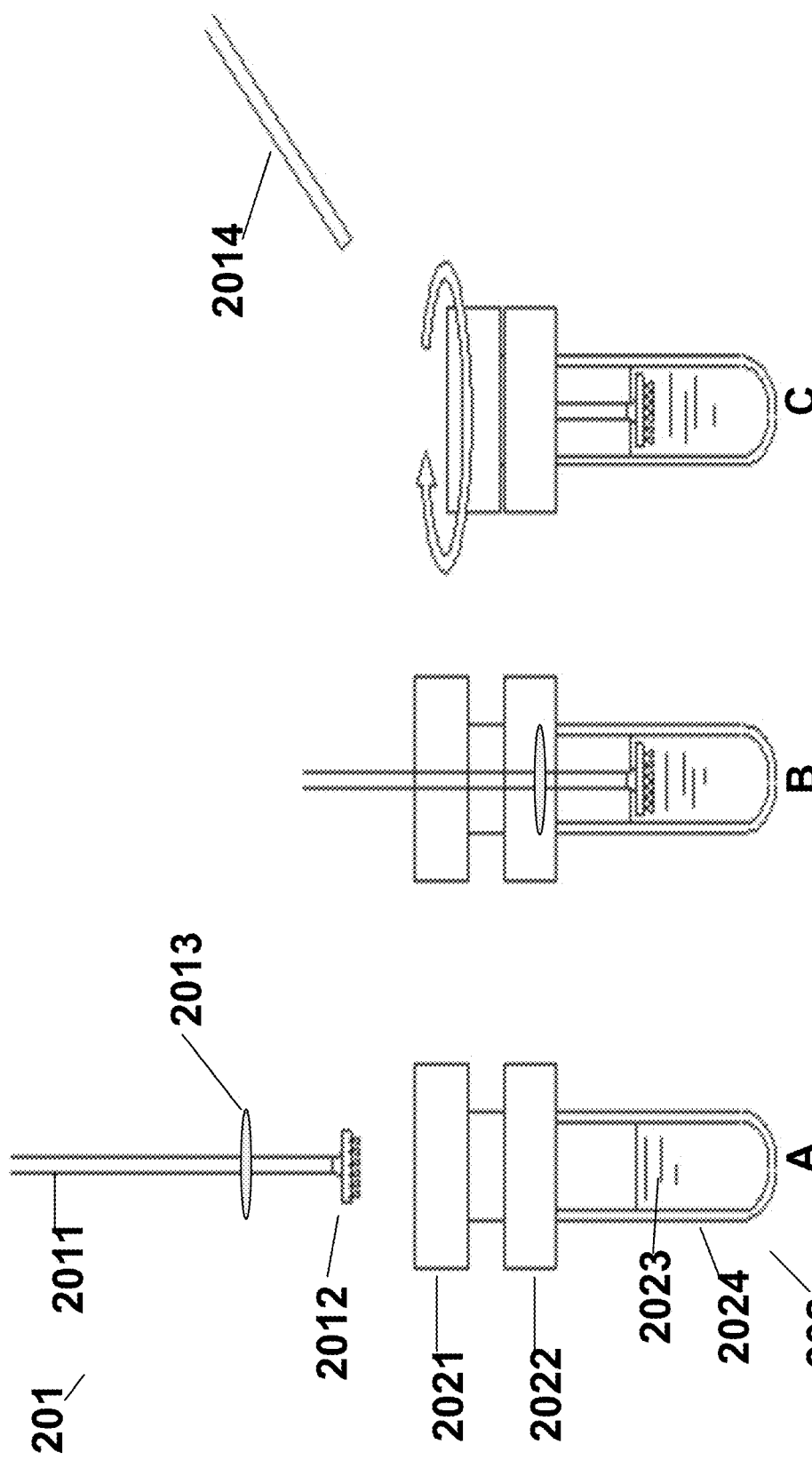
FIG. 2 (panels A-C) schematically illustrate an operation process using a device for collecting a sample as described in the present disclosure.

FIG. 2 (panel A) shows a swab 201 and a collection device 202. The collection device 202 may comprise a cap. The cap may comprise a first element 2021 fitted onto a second element 2022. The second element 2022 may be fixed (e.g., mounted) on a collection vessel 2024, and the collection vessel may comprise reagents 2023 necessary for nucleic acid amplification. The first element 2021 and the second element 2022 may comprise screw structures, so that the first element 2021 may be screwed onto the second element 2022, thereby sealing the cap and/or the collection vessel. The swab 201 may comprise a head 2012 attached to one end of a stem 2011. The stem 2011 may also include a collar 2013. FIG. 2 (panel B) shows that the swab 201 may be deposited in the collection vessel 2024 through a channel in the cap. The swab may be fixed in a position within the collection vessel via the collar 2013 so that upon the swab being deposited in the collection vessel, the stem 2011 may extend through the channel and the head 2012 may be accessed (e.g., dipped or soaked) by the reagents 2023 necessary for nucleic acid amplification. FIG. 2 (panel C) shows that by rotating the first element of the cap 2021 relative to the second element 2022 (e.g., in a clockwise or counter clockwise direction), a longitudinal portion 2014 of the stem 2011 extending beyond the cap may be severed. Upon rotation, the first element 2021 may move towards the second element 2022, thereby sealing the swab in the collection vessel.

Figure 3:
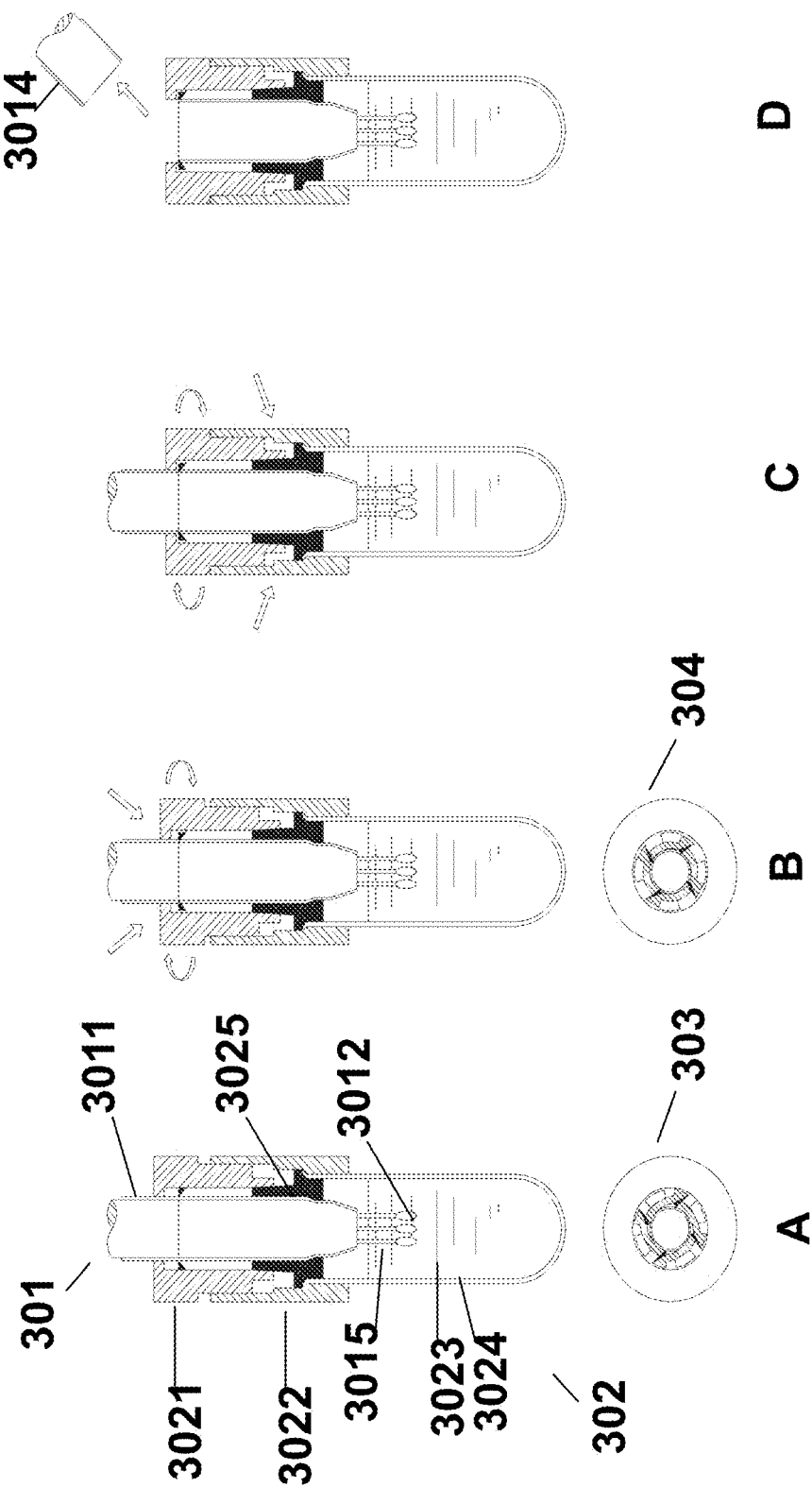
FIG. 3 (panels A-D) schematically illustrate an operation procedure using a device for collecting a sample as described in the present disclosure.

FIG. 3 (panel A) shows a sample collection member 301 deposited in a collection device 302 of the present disclosure. The sample collection member 301 may comprise two or more swabs (e.g., three or more swabs) integrated with a stem 3011. Each of the two or more swabs may comprise a head 3012 and a rod 3015, wherein the head 3012 is attached to one end of the rod 3015, while the other end of the rod is attached to an end of the stem 3011. Each of the two or more swabs may be separately integrated with the stem 3011 independent of the other swabs. The collection device 302 may comprise a cap integrated with a collection vessel 3024, wherein the collection vessel may comprise reagents 3023 necessary for nucleic acid amplification. The cap may comprise a first element 3021 fitted (e.g., screwed) onto a second element 3022, and the second element 3022 may be fixed (e.g., mounted) onto the collection vessel 3024, for example, the second element 3022 may be fixed onto the collection vessel 3024 near an opening thereof. The cap may further comprise a gasket 3025 capable of providing a seal to the collection vessel 3024 upon rotation of the cap (e.g., rotation of the first element 3021). The gasket 3025 may be fixed (e.g., partially inserted in) at the opening of the collection vessel 3024 together with the second element 3022. In certain examples, the gasket 3025 may be penetrable before or upon insertion of the sample collection member 301. In some embodiments, the gasket 3025 and the stem 3011 may be dimensioned so that movement of the sample collection member 301 towards and into the collection vessel may be blocked by the gasket 3025 (e.g., with the gasket having a smaller cross-sectional area than that of certain parts of the stem 3011). A cross sectional view 303 of the cap with the stem 3011 extending through a channel therein is also shown. In the view of 303, the channel is in an open state, wherein blades comprised in the channel are retracted, permitting insertion of the sample collection member 301 therethrough.

FIG. 3 (panel B) shows that upon rotation of the first element 3021, the blades within the channel may be actuated to move with respect to a circumference of the channel towards the center, as a result, the blades may contact with and cut the portion of the stem adjacent thereto. A cross sectional view 304 of the cap with the blades in contact with the stem is also shown.

FIG. 3 (panels C and D) show that upon further rotation of the first element 3021 relative to the collection vessel 3024, a longitudinal portion 3014 of the stem 3011 extending beyond the cap may be severed. Meanwhile, the first element 3021 may keep moving towards the second element 3022 mounted on the collection vessel 3024, thereby sealing the swab in the collection vessel.

Figure 4:
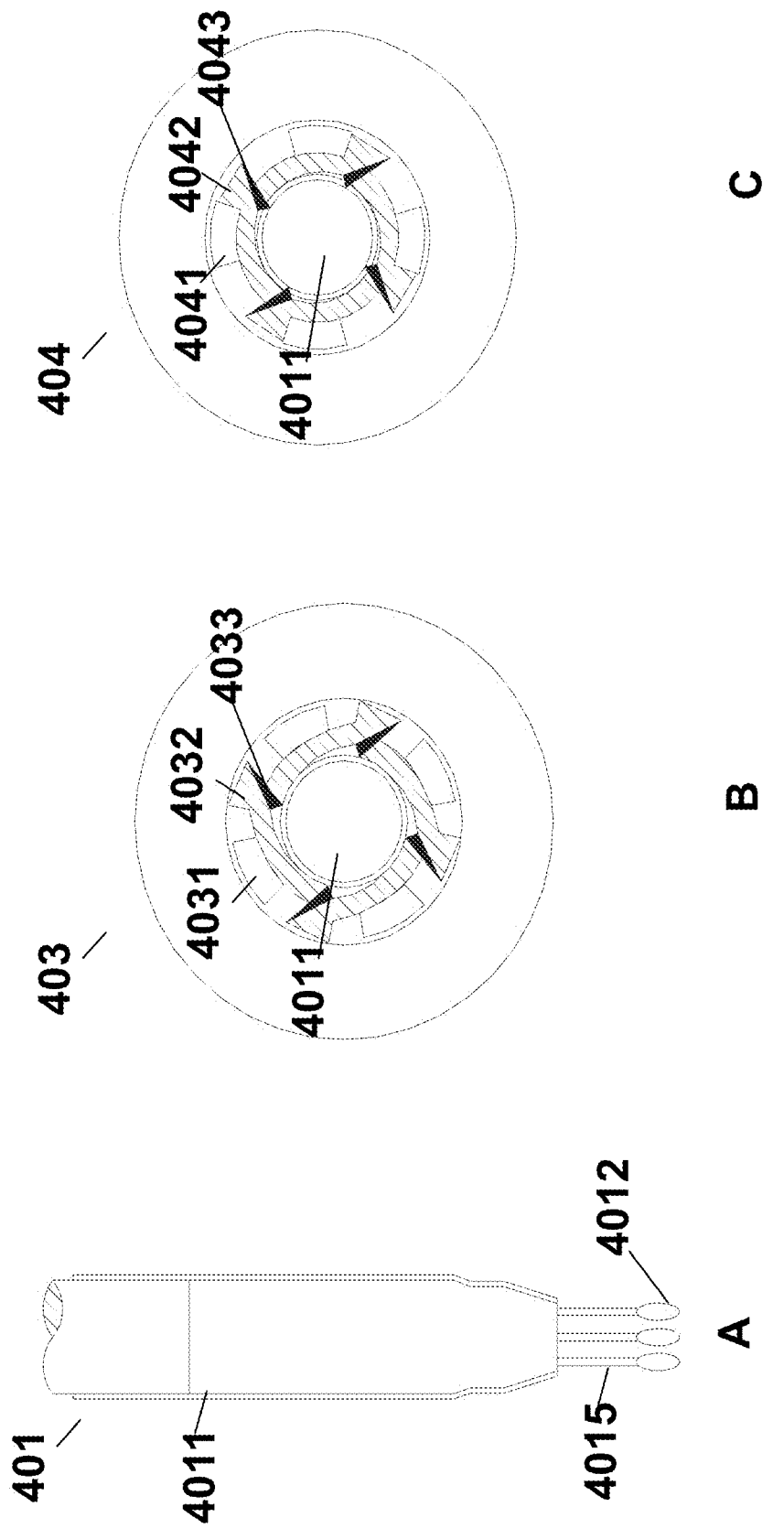
FIG. 4 (panels A-C) schematically illustrate severing a longitudinal portion of a stem (4011) with a device of the present disclosure.

FIG. 4 (panel A) shows a sample collection member 401, which may comprise two or more swabs (e.g., three or more swabs) integrated with a stem 4011. Each of the two or more swabs may comprise a head 4012 and a rod 4015, wherein the head 4012 is attached to one end of the rod 4015, while the other end of the rod is attached to an end of the stem 4011.

FIG. 4 (panel B) shows an enlarged view 403 of a cross section of a cap with the stem 4011 extending through a channel therein, and the channel is in an open state, wherein blades 4033 comprised in the channel are kept retracted, permitting insertion of the sample collection member 401 therethrough. The channel may comprise a cutting member including at least one blade 4033 (e.g., 2-4 blades). The blade may be attached to an end of an arm 4032 and the arm may be actuated to rotate with respect to the circumference of the channel with the aid of a flange 4031. As can be seen in FIG. 4 (panel C), upon rotation of a cap, a flange 4041 may be actuated to move towards and engage an arm 4042, which in turn, may drive a blade 4043 attached to an end thereof to rotate with respect to a circumference of the channel towards the center of the channel cross-section, as a result, the blades may contact with and cut the portion of the stem 4011 adjacent thereto. In certain cases, the arm 4042 may be made of elastic material so that upon being engaged by a flange 4041, the arm 4042 may be pressed towards the direction of the adjacent stem 4011, driving the blade 4043 attached to an end thereof to rotate with respect to a circumference of the channel towards the center of the channel cross-section. As a result, a longitudinal portion of the stem 4011 may be severed and the rest of the swab may be sealed within the collection device. Then, the collection device with the swab sealed therein may be used directly for further analysis (e.g., for nucleic acid amplification).

The reagents necessary for nucleic acid amplification may include, but not limited to, one or more primers and one or more polymerizing enzymes. In certain cases, the reagents may comprise Mg or Mn ions. The reagents may include one or more of the following: primer(s), probe(s), nucleotides, polymerase, reverse transcriptase, and/or amplification buffer. The reagents can include any one, two, three, four, five, or all of the primer(s), probe(s), nucleotides, polymerase, reverse transcriptase and amplification buffer. The primer(s) may have sequences that are selected to assay for a presence of a disorder or disease, such as an infectious disease, in the subject.

The one or more primers may have sequences that are selected to assay for a presence of a disorder or disease, such as an infectious disease, in the subject. The infectious agent may be associated with a disease that the subject is having, being suspected of having or at the risk of having. In some embodiments, the disease may be associated with a virus e.g., an RNA virus or a DNA virus. For example, the virus can be selected from the group consisting of human immunodeficiency virus I (HIV I), human immunodeficiency virus II (HIV II), an orthomyxovirus, Ebola virus, Dengue virus, influenza viruses, hepevirus, hepatitis A virus, hepatitis B virus, hepatitis C virus, hepatitis D virus, hepatitis E virus, hepatitis G virus, Epstein-Barr virus, mononucleosis virus, cytomegalovirus, SARS virus, West Nile Fever virus, polio virus, measles virus, herpes simplex virus, smallpox virus, adenovirus, Varicella virus, Coxsackie virus A16 (CA16), Entero virus 71 (EV71), Epstein-Barr (EB) virus, and human papilloma virus (HPV). In some embodiments, the influenza virus can be selected from the group consisting of H1N1 virus, H3N2 virus, H7N9 virus and H5N1 virus. In some embodiments, the adenovirus may be adenovirus type 55 (ADV55) or adenovirus type 7 (ADV7). In some embodiments, the hepatitis C virus may be armored RNA-hepatitis C virus (RNA-HCV). In some embodiments, the disease may be associated with a pathogenic bacterium (e.g., Mycobacterium tuberculosis) or a pathogenic protozoan (e.g., Plasmodium).

The reagents necessary for nucleic acid amplification (e.g., DNA amplification, RNA amplification) may include, but not limited to, primer sets having specificity for target RNA or target DNA, DNA produced from reverse transcription of RNA, a DNA polymerase, a reverse transcriptase (e.g., for reverse transcription of RNA), suitable buffers (including zwitterionic buffers), co-factors (e.g., divalent and monovalent cations), nucleotides, and other enzymes (e.g., uracil-DNA glycosylase (UNG)), etc). In some cases, the reagents can also comprise one or more reporter agents. The reagents can also include an enzyme that is suitable to facilitate nucleic acid amplification, e.g., a polymerizing enzyme (also "polymerase" herein). The polymerase can be a DNA polymerase for amplifying DNA. Any suitable DNA polymerase may be used, including commercially available DNA polymerases. The DNA polymerase can be capable of incorporating nucleotides to a strand of DNA in a template bound fashion. Non-limiting examples of DNA polymerases include Taq polymerase, Tth polymerase, Tli polymerase, Pfu polymerase, VENT polymerase, DEEPVENT polymerase, EX-Taq polymerase, LA-Taq polymerase, Expand polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, and variants, modified products and derivatives thereof. For certain Hot Start Polymerase, a denaturation operation at 94° C.-95° C. for 2 minutes to 10 minutes may be required, which may change the thermal profile based on different polymerases.

In some cases, a DNA sample can be generated from an RNA sample. This can be achieved using reverse transcriptase, which can include an enzyme that is capable of incorporating nucleotides to a strand of DNA, when bound to an RNA template. Any suitable reverse transcriptase may be used. Non-limiting examples of reverse transcriptases include HIV-1 reverse transcriptase, M-MLV reverse transcriptase, AMV reverse transcriptase, telomerase reverse transcriptase, and variants, modified products and derivatives thereof.

Nucleic acid amplification reaction can include one or more primer extension reactions to generate amplified product(s). In PCR, for example, a primer extension reaction can include a cycle of incubating a reaction mixture at a denaturation temperature for a denaturation duration and incubating a reaction mixture at an elongation temperature for an elongation duration. Denaturation temperatures may vary depending upon, e.g., the particular biological sample analyzed, the particular source of target nucleic acid (e.g., viral particle, bacteria) in the biological sample, the reagents used, and/or the desired reaction conditions. For example, a denaturation temperature may be from about 80° C. to about 110° C. In some examples, a denaturation temperature may be from about 90° C. to about 100° C. In some examples, a denaturation temperature may be from about 90° C. to about 97° C. In some examples, a denaturation temperature may be from about 92° C. to about 95° C. In still other examples, a denaturation temperature may be at least about 80°, 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C.

As an alternative, in isothermal amplification, the temperature can be fixed (i.e., maintained constant and not cycled), and amplification product(s) can be generated using a primer set and a polymerase with high strand displacement activity in addition to a replication activity. An example of a polymerase that may be suitable for use in isothermal amplification is Bst polymerase. The temperature can be fixed between about 50° C. and 80° C., or 60° C. and 65° C. In loop mediated isothermal amplification (LAMP), e.g., a template nucleic acid molecule can be amplified using a polymerase and a primer set having at least 2, 3, 4, or 5 primers.

The amplification of the template nucleic acid molecule and detection of the target nucleic acid molecule can be performed in the same system, e.g., a vessel. In some cases, the system is a tube that is configured for nucleic acid amplification, e.g., an eppendorf PCR tube.

Method for Collecting a Sample of a Subject

Another aspect of the present disclosure provides methods for collecting a sample (e.g., a tissue sample, such as a sample comprising oral epithelium cells) of a subject. A method for collecting a sample for nucleic acid amplification may comprise providing a collection device comprising a collection vessel that may include reagents necessary for nucleic acid amplification. The collection vessel may be adapted to accept at least one swab containing the sample. The collection device may further comprise a cap integrated with the collection vessel and having a channel extending therethrough to permit the at least one swab to be deposited in the collection vessel. The channel may be closable upon rotation of the cap. The collection device may also comprise at least one cutting member that severs a longitudinal portion of a stem of the swab extending through the channel upon rotation of the cap. The collection vessel and/or the cap may be dimensioned such that upon depositing the swab in the collection vessel, the stem of the swab extends through the channel. The collection device may be a device as described elsewhere in the present disclosure.

Next, the swab having the sample from the subject may be provided in the collection vessel. For example, the swab can be used to collect a sample from the subject (e.g., cheek swab) and the swab can be subsequently deposited (e.g., inserted) in the collection vessel. In some examples, the subject or another individual (e.g., doctor) uses the swab to collect the sample from the subject. The swab may be a swab as described elsewhere in the present disclosure.

Next, with the swab provided in the collection vessel, the cap may be rotated (e.g., clockwise). Upon rotation of the cap, the cutting member may sever a longitudinal portion of the stem of the swab extending through the channel to provide the swab sealed in the collection vessel and in contact with the reagents necessary for nucleic acid amplification. For example, after depositing at least one swab in the collection vessel (e.g., upon contacting of the swab with reagents contained in the collection vessel), the cap (or a portion/element thereof) may be rotated (e.g., counter clockwise), rotation of the cap or a portion thereof may actuate a cutting member (e.g., a blade) comprised in the channel contained in the cap to move with respect to a circumference of the channel towards the center, as a result, the cutting member may contact with and cut the portion of the swab stem adjacent thereto. Then, after a portion of the stem extending beyond the cap is severed with rotation of the cap (or a portion/element thereof), the cap (or a portion/element thereof) may keep moving towards the collection vessel, thereby sealing the rest of the swab in the collection vessel.

Next, nucleic acid amplification may be performed on the sample. Performing the nucleic acid amplification may comprise subjecting a reaction mixture having the biological sample or the nucleic acid sample to nucleic acid amplification conditions comprising at least one heating and cooling cycle. Examples of nucleic acid amplification methods are described in, for example, PCT/CN2013/090425, PCT/CN2014/094914, PCT/CN2014/095987 each of which is entirely incorporated herein by reference. The nucleic acid amplification conditions may comprise cycling a temperature of a reaction mixture having the biological sample or the nucleic acid sample between at least two different temperatures. In some cases, the nucleic acid amplification conditions may comprise cycling a temperature of a reaction mixture having the biological sample or the nucleic acid sample between at least three different temperatures. In some embodiments, the nucleic acid amplification conditions may comprise cycling a temperature of a reaction mixture having the biological sample or the nucleic acid sample between a denaturing temperature, annealing temperature and elongation temperature.

Nucleic acid amplification may assay for a presence or absence of one or more targets in the sample. Upon performing nucleic acid amplification, a report may be generated that is indicative of the presence or absence of the one or more targets. The report may be an electronic report (e.g., electronic mail, instant message, text message, user interface element, or electronic document) or a physical report (e.g., paper report). The report may be directed to the subject or another individual (e.g., healthcare professional) over a network.

The collection device may be sealed with a sealing member (e.g., a plug) before a swab is deposited in the collection vessel. For example, the sealing member may be comprised in the cap (e.g., forming a part of the cap, for example, being inserted into the channel comprised by the cap). When the sealing member is in place, the channel may be closed and the cap may be sealed and contents contained in the collection vessel (e.g., reagents necessary for nucleic acid amplification) will be kept away from the surrounding environment (e.g., substances in the air, potential contaminants). Before depositing a swab in the collection vessel, the sealing member may be removed (e.g., by pulling it away from the cap) so as to open the cap (e.g., by opening the channel in the cap), thereby permitting the swab to be inserted into the collection vessel through the open cap. The sealing member may be made from a variety of materials, such as paper, rubber, silicone, metal, cork, felt, neoprene, nitrile rubber, fiberglass, polytetrafluoroethylene (also known as PTFE or Teflon) or other polymeric materials, such as a plastic polymer (e.g., polychlorotrifluoroethylene).

The sample can comprise tissues or cells obtained from nose, pharynx, ear, eye, throat, mouth, bucca, cervix, vagina, skin wound, urethra or other body parts of a subject. The sample can be obtained directly from the subject, for example, the sample can be analyzed or tested (e.g., by amplification or sequencing) without further processing (e.g., by extraction, centrifugation, purification, etc.).

The nucleic acid amplification can be performed using the sample (e.g., the tissue sample) deposited in the collection vessel. For example, the tissue sample that is deposited in the collection vessel can be subjected to nucleic acid amplification conditions (e.g., PCR) without any additional processing (e.g., extraction, purification, centrifugation etc.).

The reagents comprised in the collection vessel can include, but not limited to, one or more primers and one or more polymerizing enzymes. In certain cases, the reagents may comprise Mg or Mn ions. The reagents may include one or more of the following: primer(s), probe(s), nucleotides, polymerase, reverse transcriptase, and/or amplification buffer. The reagents can include any one, two, three, four, five, or all of the primer(s), probe(s), nucleotides, polymerase, reverse transcriptase and amplification buffer. The primer(s) may have sequences that are selected to assay for a presence of a disorder or disease, such as an infectious disease, in the subject.

The one or more primers may have sequences that are selected to assay for a presence or quantity of an infectious agent in said subject. The infectious agent may be associated with a disease that the subject is having, being suspected of having or at the risk of having. In some embodiments, the disease may be associated with a virus e.g., an RNA virus or a DNA virus. For example, the virus can be selected from the group consisting of human immunodeficiency virus I (HIV I), human immunodeficiency virus II (HIV II), an orthomyxovirus, Ebola virus, Dengue virus, influenza viruses, hepevirus, hepatitis A virus, hepatitis B virus, hepatitis C virus, hepatitis D virus, hepatitis E virus, hepatitis G virus, Epstein-Barr virus, mononucleosis virus, cytomegalovirus, SARS virus, West Nile Fever virus, polio virus, measles virus, herpes simplex virus, smallpox virus, adenovirus, and Varicella virus. In some embodiments, the influenza virus can be selected from the group consisting of H1N1 virus, H3N2 virus, H7N9 virus and H5N1 virus. In some embodiments, the adenovirus may be adenovirus type 55 (ADV55) or adenovirus type 7 (ADV7). In some embodiments, the hepatitis C virus may be armored RNA-hepatitis C virus (RNA-HCV). In some embodiments, the disease may be associated with a pathogenic bacterium (e.g., Mycobacterium tuberculosis) or a pathogenic protozoan (e.g., Plasmodium).

The swab or sample collection member can be part of the collection device. For example, the swab or sample collection member can be grouped or packaged together with the collection device, or integrated into the collection device, e.g., in a reversible way.

Methods of the present disclosure may be performed in a time period from about 1 minute to 120 minutes, 1 minute to 60 minutes, or 1 minute to 30 minutes. In some embodiments, the time period is less than about 6 hours, less than about 3 hours, less than about 1 hour, less than about 30 minutes, less than about 20 minutes, less than about 10 minutes, less than about 5 minutes, less than about 3 minutes, less than about 1 minute, or less than about 30 seconds. For example, a sample can be collected form a subject, deposited in a collection vessel and the collection vessel can be subsequently sealed in a time period that is less than about 1 minute or 30 seconds.

The source of the sample can be a pool of the sample in a storage vessel. The source may also be a tissue of the subject that is accessible with a sample collection member, such as a swab.

A collection device as illustrated in FIG. 2 may be used for sample collection. A collection device 202 may be provided to a subject (e.g., a human individual suspected of being infected with a pathogen). The collection device 202 may comprise a cap. The cap may comprise a first element 2021 fitted onto a second element 2022. The second element 2022 may be fixed (e.g., mounted) on a collection vessel 2024, and the collection vessel may comprise reagents 2023 necessary for nucleic acid amplification (e.g., reagents necessary for amplifying nucleic acid associated with the presence or absence of a suspected pathogen). The first element 2021 and the second element 2022 may comprise screw structures, so that the first element 2021 may be screwed onto the second element 2022, thereby sealing the cap and/or the collection vessel. In some embodiments, the cap (or the first element 2021 comprised by the cap) may further comprise a plug, which may be inserted into the channel within the cap, thereby sealing the cap and keeping the contents contained in the collection vessel away from substances in the surrounding environment.

The subject may be provided with a swab 201 for collecting a sample, the swab may be provided prior to, at the same time with, or after providing the collection device 202. The swab 201 may comprise a head 2012 attached to one end of a stem 2011. The stem 2011 may also include a collar 2013 capable of engaging with a channel in the cap to provide the stem extending through the channel when the swab is deposited in the collection vessel. The head 2012 may be pivotable with respect to the stem 2011. For example, the stem 2011 and head 2012 may be coupled at a pivot joint that enables the head 2012 to pivot or rotate with respect to the stem 2011. As an alternative, the head 2012 is not pivotable with respect to the stem 2011.

The swab or a part of the swab comprising the head 2012 may be actuated (e.g., by the subject or a person assisting the subject, such as a medical professional) to get into contact with a sample (e.g., oral epithelium), thereby collecting the sample (e.g., by scraping a tissue surface with the swab). Then, a plug sealing the cap of the collection device may be removed (e.g., being pulled away from the cap, such as being pulled out of a channel in the cap), the channel within the cap will then be open, allowing the swab containing the sample to be inserted through the open channel into the collection vessel. When the head 2012 comprising the sample is in contact with the reagents 2023 necessary for nucleic acid amplification contained in the collection vessel 2024, movement of the swab along the length of the collection vessel may be stopped, e.g., with the aid of the collar 2013. In an example, the collar 2013 may be configured to engage with a specific portion of the channel by contacting with and pressing against the wall of that specific portion of the channel (e.g., applying a force to the wall of the channel in a direction roughly perpendicular to the direction of movement of the swab), thereby creating a frictional force at the interface between the collar and the channel wall, which in turn may block further movement of the swab along the length of the channel.

After the swab reaches and is fixed at the desired position, the first element of the cap 2021 may be rotated relative to the second element 2022 (e.g., in a clockwise direction). This rotation of the first element of the cap 2021 may actuate a cutting member (e.g., a blade) within the cap to rotate with respect to a circumference of the channel towards the center of the channel; as a result, the cutting member may contact with and cut the portion of the stem 2011 adjacent thereto. Then, a longitudinal portion 2014 of the stem 2011 extending beyond the cap may be severed. Upon further rotation, the first element 2021 may continue to move towards the second element 2022, thereby sealing the rest of the swab in the collection device.

Then, the collection device with the swab sealed therein may be used directly for further analysis (e.g., for nucleic acid amplification). In an example, the further analysis is performed by PCR.

In one example, before loading the collection vessel in a machine for performing PCR, the cap may be removed together with the swab. This may be carried out after the sample has been sufficiently deposited (e.g., dissolved, dispersed) in the reagents contained in the collection vessel. In some embodiments, after removing the swab and the cap, another sealing member (e.g., a cover, a plug or another cap) may be additionally provided to seal the collection vessel containing the reagents and the sample.

In another example, PCR may be carried out without opening the collection vessel, and it may not be necessary to remove the swab sealed in the collection vessel before performing PCR.

Kits for Nucleic Acid Amplification

Another aspect of the present disclosure provides kits for nucleic acid amplification. A kit may comprise a collection device. The collection device may comprise a collection vessel that includes reagents necessary for nucleic acid amplification. The reagents can be as described elsewhere in the present disclosure. In some cases, the reagents include one or more of the following: primer(s), probe(s), nucleotides (e.g., nucleotide triphosphates containing deoxyribose, or dNTP), polymerizing enzyme (or polymerase), reverse transcription enzyme (or reverse transcriptase), and/or amplification buffer. The reagents can include any one, two, three, four, five, or all of the primer(s), probe(s), nucleotides, polymerizing enzyme, reverse transcription enzyme and amplification buffer. The one or more primers may have sequences that are selected to assay for a presence of disorder or disease, such as an infectious disease, in a subject.

The collection vessel may be adapted to accept at least one swab. The collection device may further comprise a cap integrated with the collection vessel. The cap may have a channel extending therethrough to permit at least one swab to be deposited in the collection vessel. The channel may be closable upon rotation of the cap. The collection device may also comprise at least one cutting member. The cutting member may be capable of severing a longitudinal portion of a stem of the at least one swab extending through the channel upon rotation of the cap. The collection vessel and/or the cap may be dimensioned such that upon depositing the at least one swab in the collection vessel, the stem of the swab may extend through the channel. The collection device may be as described elsewhere in the present disclosure.

The kit may also comprise the at least one swab. The at least one swab may include one or more swabs, e.g., at least 2 swabs, at least 3 swabs, at least 4 swabs, at least 5 swabs, etc. When there are two or more swabs, the swabs may be integrated with the stem. When there are two or more swabs, each of the two or more swabs may be integrated with the same stem via a separate rod projecting from the stem, therefore, one end of the rod may be connected to the stem while the other end of the rod may be connected to a swab. The at least one swab may be positioned in a package or container of the kit. In some embodiments, the at least one swab may be packaged together with the collection device in the kit.

The kit may further comprise instructions that permit a user to use the at least one swab to collect a biological sample from a source of the sample. The instructions may also permit a user to deposit the at least one swab having the biological sample into the collection vessel to provide a reaction mixture comprising the biological sample and the reagents necessary for nucleic acid amplification. The instructions may be printed on paper or provided digitally, such as on a universal serial bus (USB) device or made accessible over a network. The instructions may permit a user to perform nucleic acid amplification using the biological sample.

The instructions may permit a user to (a) use the at least one swab to collect a biological sample from a source of the sample, and (b) deposit the at least one swab having the biological sample into the collection vessel to provide a reaction mixture comprising the biological sample and the reagents necessary for nucleic acid amplification in a time period of less than about 1 hour, e.g., less than about 50 minutes, less than about 40 minutes, less than about 30 minutes, less than about 20 minutes, less than about 15 minutes, less than about 10 minutes, less than about 5 minutes, less than about 4 minutes, less than about 3 minutes, less than about 2 minutes, less than about 1 minute, less than about 50 seconds, less than about 40 seconds, less than about 30 seconds, less than about 20 seconds, or less than about 10 seconds. For example, the time period can be in about 10 seconds-30 seconds, in about 1 minute-5 minutes, in about 1 minute-10 minutes, in about 1 minute-15 minutes, in about 1 minute-20 minutes, in about 1 minute-30 minutes, in about 1 minute-40 minutes, in about 1 minute-50 minutes or in about 1 minute-60 minutes.

The instructions may be in textual form, graphical form, or textual and graphical form. The instructions can be in a physical medium (e.g., paper) or an electronic medium (e.g., computer memory). The instructions can include one or more operations that a user may follow to perform nucleic acid amplification using the sample.

The kit may include a package or container. The kit may include a box (e.g., recyclable box) that includes a collection device, at least one swab and instructions. The kit can include identifying information, which can permit the kit to be identified and/or associated with a user. In some cases, the identifying information permits the kit to be anonymously associated with the user. The identifying information can be a barcode or a radio-frequency identification (RFID) tag.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents.

What is claimed is:

1. A device for collecting a sample from a subject for nucleic acid amplification, comprising:
   a collection vessel that includes reagents necessary for nucleic acid amplification, wherein said collection vessel is adapted to accept at least one swab containing said sample;
   a cap integrated with said collection vessel and having a channel extending therethrough to permit said at least one swab to be deposited in said collection vessel, wherein said channel is closable upon rotation of said cap; and
   at least one cutting member that severs a longitudinal portion of a stem of said at least one swab extending through said channel upon rotation of said cap,
   wherein said collection vessel and/or said cap are dimensioned such that upon depositing said at least one swab in said collection vessel, said stem of said at least one swab extends through said channel, and
   wherein upon rotation of said cap, said at least one cutting member severs a longitudinal portion of said stem of said at least one swab extending through said channel to provide said at least one swab sealed in said collection vessel and in contact with said reagents necessary for nucleic acid amplification.

2. The device of claim 1, wherein rotation of said cap provides a hermetic seal to said collection vessel.

3. The device of claim 1, wherein said at least one cutting member is integrated with said cap.

4. The device of claim 1, wherein said stem of said at least one swab includes a collar capable of engaging with said channel to provide said stem extending through said channel when said at least one swab is deposited in said collection vessel.

5. The device of claim 1, wherein said cap includes a gasket that provides a seal to said collection vessel upon rotation of said cap.

6. The device of claim 1, wherein said at least one cutting member includes at least one blade.

7. The device of claim 6, wherein said at least one cutting member is in said channel.

8. The device of claim 6, wherein said at least one blade is rotatable with respect to a circumference of said channel.

9. The device of claim 6, wherein said at least one blade includes at least two blades.

10. The device of claim 1, wherein said at least one swab includes at least two swabs.

11. The device of claim 10, wherein said at least one swab includes at least five swabs.

12. The device of claim 10, wherein said at least two swabs are integrated with said stem.

13. The device of claim 1, wherein rotation of said cap seals said channel.

14. The device of claim 13, wherein upon rotation of said cap to seal said channel, said cap moves towards said collection vessel.

15. The device of claim 1, wherein said collection vessel includes identifying information of said subject.

16. The device of claim 15, wherein said identifying information is encoded in a barcode.

17. The device of claim 15, wherein said identifying information is encoded in a radio-frequency identification (RFID) tag.

18. The device of claim 1, wherein said collection vessel includes identifying information that anonymously identifies said bodily fluid sample from said subject.

19. The device of claim 1, wherein said reagents include one or more primers and a polymerizing enzyme.

20. The device of claim 19, wherein said reagents include magnesium (Mg) or manganese (Mn) ions.

21. The device of claim 19, wherein said one or more primers have sequences that are configured to assay for a presence of an infectious disease in said subject.

22. A method for collecting a biological sample from a subject for nucleic acid amplification, comprising:
   (a) providing a collection device comprising (i) a collection vessel that includes reagents necessary for nucleic acid amplification, wherein said collection vessel is adapted to accept at least one swab containing said biological sample, (ii) a cap integrated with said collection vessel and having a channel extending therethrough to permit said at least one swab to be deposited in said collection vessel, wherein said channel is closable upon rotation of said cap, and (iii) at least one cutting member that severs a longitudinal portion of a stem of said at least one swab extending through said channel upon rotation of said cap, wherein said collection vessel and/or said cap are dimensioned such that upon depositing said at least one swab in said collection vessel, said stem of said at least one swab extends through said channel;
   (b) depositing said at least one swab having said biological sample from said subject in said collection vessel, and
   (c) rotating said cap, wherein upon rotation of said cap, said at least one cutting member severs a longitudinal portion of said stem of said at least one swab extending through said channel to provide said at least one swab sealed in said collection vessel and in contact with said reagents necessary for nucleic acid amplification.

23. A kit for nucleic acid amplification, comprising:
   a collection device comprising (i) a collection vessel that includes reagents necessary for nucleic acid amplification, wherein said collection vessel is adapted to accept at least one swab, (ii) a cap integrated with said collection vessel and having a channel extending therethrough to permit said at least one swab to be deposited in said collection vessel, wherein said channel is closable upon rotation of said cap, and (iii) at least one cutting member that severs a longitudinal portion of a stem of said at least one swab extending through said channel upon rotation of said cap, wherein said collection vessel and/or said cap are dimensioned such that upon depositing said at least one swab in said collection vessel, said stem of said at least one swab extends through said channel; and
   instructions that permit a user to (a) collect a biological sample from a source of said sample using said at least one swab, and (b) deposit said at least one swab having said biological sample into said collection vessel to provide a reaction mixture comprising said biological sample and said reagents necessary for nucleic acid amplification.

* * * * *